(12) United States Patent
Bonin et al.

(10) Patent No.: US 6,906,799 B2
(45) Date of Patent: Jun. 14, 2005

(54) SIGNAL PROCESSING METHOD FOR IN-SITU, SCANNED-BEAM PARTICLE MONITORING

(75) Inventors: Michel P. Bonin, Danville, CA (US); Aaron Stibbich, Livermore, CA (US); Donald J. Holve, Berkeley, CA (US)

(73) Assignee: Inficon, Inc., East Syracuse, NY (US)

( * ) Notice: Subject to any disclaimer, the term of this patent is extended or adjusted under 35 U.S.C. 154(b) by 141 days.

(21) Appl. No.: 10/237,458

(22) Filed: Sep. 9, 2002

(65) Prior Publication Data

US 2003/0076494 A1 Apr. 24, 2003

Related U.S. Application Data (60) Provisional application No. 60/318,073, filed on Sep. 7, 2001.

(51) Int. Cl.[7] ............................................... G01N 15/02
(52) U.S. Cl. ..................................................... 356/336
(58) Field of Search ................................ 356/356, 457, 356/337–343, 436–440, 39–43; 250/573, 574, 436, 578.1

(56) References Cited

U.S. PATENT DOCUMENTS

| | | |
|---|---|---|
| 4,260,258 A | 4/1981 | Rose et al. |
| 4,473,296 A | 9/1984 | Shofner et al. |
| 4,571,079 A | 2/1986 | Knollenberg |
| 4,636,075 A | 1/1987 | Knollenberg |
| 4,697,925 A | 10/1987 | Hyodo et al. |
| 4,728,190 A | 3/1988 | Knollenberg |
| 4,739,177 A | 4/1988 | Borden |
| 4,783,599 A | 11/1988 | Borden |
| 4,792,199 A | 12/1988 | Borden |
| 4,798,465 A | 1/1989 | Knollenberg |
| 4,804,853 A | 2/1989 | Borden et al. |
| 4,812,664 A | 3/1989 | Borden |
| 4,825,094 A | 4/1989 | Borden et al. |
| 4,827,144 A | 5/1989 | Zaitsu et al. |
| 4,885,473 A | 12/1989 | Shofner et al. |
| 4,887,213 A * | 12/1989 | Smart et al. .................... 701/3 |
| 4,893,928 A | 1/1990 | Knollenberg |
| 4,894,529 A | 1/1990 | Borden et al. |
| 4,896,048 A | 1/1990 | Borden |
| 4,906,094 A | 3/1990 | Ashida |
| 4,917,496 A | 4/1990 | Sommer |
| 4,920,275 A | 4/1990 | Itoh |
| RE33,213 E | 5/1990 | Borden |
| 4,984,889 A | 1/1991 | Sommer |
| 5,011,286 A | 4/1991 | Petralli |
| 5,033,851 A | 7/1991 | Sommer |
| 5,037,202 A | 8/1991 | Batchelder et al. |
| 5,055,698 A | 10/1991 | Borden |
| 5,061,065 A | 10/1991 | Sommer |
| 5,061,070 A | 10/1991 | Batchelder et al. |
| 5,083,865 A | 1/1992 | Kinney et al. |
| 5,085,500 A | 2/1992 | Blesener |
| 5,092,675 A | 3/1992 | Sommer |

(Continued)

FOREIGN PATENT DOCUMENTS

EP   0 539 022 A2   4/1993

*Primary Examiner*—Tu T. Nguyen
(74) *Attorney, Agent, or Firm*—Wall Marjama & Bilinski LLP (57) ABSTRACT

A novel method for analyzing the pulse train resulting from a scanned beam particle monitor is described. The method enhances signal-to-noise ratio and significantly reduces particle false alarm rate. Performed in the time domain, the method filters noise pulses that do not occur at the scanner frequency. The analysis further identifies particle-pulse-envelopes (PPE's) by performing a forward-looking and backward-looking autocorrelation. Gaussian fits are subsequently applied to identified particle-pulse envelopes, to determine particle characteristics, such as size and speed.

33 Claims, 11 Drawing Sheets

U.S. PATENT DOCUMENTS

| | | |
|---|---|---|
| 5,106,187 A | 4/1992 | Bezanson |
| 5,132,548 A | 7/1992 | Borden et al. |
| 5,135,306 A | 8/1992 | Kanebako et al. |
| 5,146,098 A | 9/1992 | Stack |
| 5,153,674 A | 10/1992 | Böbel et al. |
| 5,172,004 A | 12/1992 | Furuya |
| 5,185,641 A | 2/1993 | Igushi et al. |
| 5,192,870 A | 3/1993 | Batchelder et al. |
| H1183 H | 5/1993 | Zitko et al. |
| 5,212,580 A | 5/1993 | Coad et al. |
| 5,229,839 A | 7/1993 | Hayashi et al. |
| 5,231,378 A | 7/1993 | Dennis et al. |
| 5,235,625 A | 8/1993 | Stolz et al. |
| 5,247,188 A | 9/1993 | Borden |
| 5,255,089 A | 10/1993 | Dybas et al. |
| 5,256,886 A | 10/1993 | Wolf et al. |
| 5,257,087 A | 10/1993 | Furuya |
| 5,262,841 A | 11/1993 | Blesener et al. |
| 5,266,798 A | 11/1993 | Borden et al. |
| 5,271,264 A | 12/1993 | Chanayem |
| 5,282,151 A | 1/1994 | Knollenberg |
| 5,294,806 A | 3/1994 | Batchelder et al. |
| 5,316,983 A | 5/1994 | Fujimori et al. |
| 5,347,138 A | 9/1994 | Aqui et al. |
| 5,360,980 A | 11/1994 | Borden et al. |
| 5,365,559 A | 11/1994 | Hsueh et al. |
| 5,406,830 A | 4/1995 | Borden et al. |
| 5,424,558 A | 6/1995 | Borden et al. |
| 5,428,443 A | 6/1995 | Kitamura et al. |
| 5,436,465 A | 7/1995 | Borden et al. |
| 5,438,420 A | 8/1995 | Harwick et al. |
| 5,456,102 A | 10/1995 | Moorehead |
| 5,459,569 A | 10/1995 | Knollenberg et al. |
| 5,463,460 A | 10/1995 | Fishkin et al. |
| 5,467,188 A | 11/1995 | Miyashita |
| 5,471,298 A | 11/1995 | Moriya |
| 5,481,357 A | 1/1996 | Ahsan et al. |
| 5,534,706 A | 7/1996 | Borden et al. |
| 5,565,985 A | 10/1996 | Fishkin et al. |
| 5,606,418 A | 2/1997 | Borden et al. |
| 5,621,523 A | 4/1997 | Oobayashi et al. |
| 5,637,881 A | 6/1997 | Burghard et al. |
| 5,671,046 A | 9/1997 | Knowlton |
| 5,751,422 A | 5/1998 | Mitchell |
| 5,870,189 A | 2/1999 | Uesugi et al. |
| 5,939,727 A | 8/1999 | Sommer |
| 5,943,130 A | 8/1999 | Bonin et al. |
| 6,011,622 A | 1/2000 | Fishkin et al. |
| 6,034,769 A | 3/2000 | Yufa |
| 6,072,187 A | 6/2000 | Borden et al. |
| 6,125,789 A | 10/2000 | Gupta et al. |

* cited by examiner

SIGNAL PROCESSING METHOD FOR IN-SITU, SCANNED-BEAM PARTICLE MONITORING

This application claims priority upon a provisional patent application, application Ser. No. 60/318,073, filed Sep. 7, 2001.

FIELD OF THE INVENTION

This invention relates to the field of semiconductor wafer processing, and more particularly to a method for analyzing the signals resulting from a scanned beam particle monitor.

BACKGROUND OF THE INVENTION

In-situ particle monitoring (ISPM) sensors can provide continuous monitoring of particulate contamination levels during key semiconductor process operations. Based upon light-scattering detection techniques, ISPM sensors are typically installed downstream of the process chamber, such as to a pump-line, and provide real-time measurement of variations in particle concentration and size during wafer processing. However, there are several inherent disadvantages to pump-line installation of a sensor apparatus. First, a particle depositing on a processed wafer cannot be measured with the sensor in the pump-line configuration. Second, and because ISPM sensors depend on various particle transport mechanisms to detect the particles generated upstream in the process chamber, ISPM sensor applications often produce poor correlation with the number of particles that deposit directly on the product wafer surface. In addition, the particle detection volume for ISPM sensors is also limited by the small cross-sectional area of the laser beam which is illuminating the particle (s).

To improve the correlation between ISPM sensors and the number of particles that deposit on the wafer surface, an advanced above wafer in-situ particle monitoring (hereinafter AWISPM) sensor has been developed. As described in U.S. Pat. No. 5,943,130, the entire contents of which are herein incorporated by reference, an AWISPM sensor is capable of monitoring particulate contamination levels within the process chamber. The sensor incorporates a scanned laser beam to create a large detection volume compared to stationary laser beam systems previously known to ISPM sensor technologies. Since the detection volume is only approximately 4 mm above the wafer surface, the capture rate of the AWISPM sensor is enhanced for particles that will deposit directly upon the wafer surface. The capture rate for particulate contamination is also improved by the larger detection volume, which provides a significant increase in the volumetric sampling rate. The AWISPM sensor provides information regarding the actual count, size, and velocity (speed) of the detected particles.

Because a scanned laser beam is used to detect the presence of the particle (s), a particle will be detected multiple times as it passes through the measurement volume, if the particle drift velocity is small compared with the laser beam velocity at the sample volume. Laser scanning is accomplished using either a resonant scanner or a rotating polygonal mirror. Either optical device results in a precisely defined period (e.g., frequency) associated with the scanned beam.

This defined period forms the basis of the present invention, allowing the detection and isolation of particle-pulse-envelopes (PPE's) from the continuous stream of low level electronic and optical noise (stray light) that is typically included in the observed signal. The principle contribution of the signal-processing algorithm is a substantial decrease in the level of false alarm counts at the minimum particle size detectability limit. Since the data stream is analyzed in the time domain relative to the scan frequency, PPE detection at or near signal-to-noise ratios of one can be accomplished.

SUMMARY OF THE INVENTION

It is a primary object of the present invention to overcome the above-noted deficiencies of the prior art.

It is another primary object of the present invention to eliminate or substantially reduce the incidence of false negatives occurring in a measurement volume using a scanning light source/detection apparatus.

Therefore and according to one preferred aspect of the present invention, there is provided a process for processing a scattered light signal to determine the presence of particles in a scanned measurement volume, said method comprising the steps of:

applying a scanning light beam onto a measurement volume;

detecting scattered light pulses from particles moving through said measurement volume; and processing the detected light pulses, said processing steps including the step of determining the existence of multiple pulses representative of a scanned particle in a time domain by generating a corresponding particle pulse envelope (PPE) in order to segregate particles moving in the measurement volume from noise.

Preferably, and in practice, the light pulse that is scattered by each scanned particle crossing through the measurement volume is initially detected by a photo-multiplier. The electrical current output from the photo-multiplier is then converted by conventional means into a voltage pulse, which is subsequently amplified such as for example, by means of a high-speed, two stage analog amplifier. A level-triggering device, such as a discriminator, eliminates those signals that do not exceed a minimum threshold value.

The pulse train exiting the discriminator is analyzed with a peak-detector to determine the maximum value of the pulse. This value, as well as the pulse time stamp (microsecond resolution) is stored, for example, on a computer hard disk or in the memory of a microprocessor, for post processing using a preferred signal-processing technique which is described below.

The signal processing method of the present invention is comprised of three primary functions: 1) noise removal through analysis in the time domain; 2) identification of particle-pulse envelopes (PPEs) through forward and reverse autocorrelation; and 3) Gaussian fitting to each particle-pulse envelope for particle size and speed estimates. PPE identification through forward and reverse autocorrelation is particularly important since it facilitates identification of singular particle scattering events. Achieving these count statistics is a primary objective of AWISPM sensor measurement.

An individual pulse can be confirmed as being either signal or noise by determining whether or not it is part of a PPE. This determination is accomplished by looking ahead and behind the pulse (in the time domain) for a second pulse that lags or leads within the scanner frequency.

After the removal of noise pulses, the signal-processing algorithm begins searching for PPE's. An autocorrelation calculation in the forward and reverse directions (again in the time domain) is used to identify the beginning and end of an individual PPE. At the start of the PPE, the autocorrelation is high in the forward direction and zero in the reverse autocorrelation. At the end of the envelope, autocorrelation is high in the reverse direction and zero in the forward direction. Through this approach, the beginning and end of a pulse envelope (particle) can be identified.

After the pulse envelope has been identified, a Gaussian fitting routine is applied. The algorithm begins with an assumed Gaussian mean, width, and amplitude. Each of these values are subsequently iterated to produce minimum error between the peak pulse amplitudes and the value of the Gaussian fit.

The Gaussian fit is crucial to the determination of particle characteristics, such as size and velocity. Once the fit of an envelope is obtained, the peak amplitude of the Gaussian fit is used to determine particle size while the slope of the Gaussian fit coupled with the diameter of the laser beam at the measurement volume together are used to determine particle velocity.

According to a preferred version of the invention, it has also been learned that by setting the discrimination level to at least three times and preferably four times the level of background noise will significantly reduce the number of false negatives that are detected which is essential to better determine the existence of single pulse events (e.g., particles which are contacted only a single time by the scanned beam).

Other objects, features and advantages will become readily apparent from the following Detailed Description which should be read in conjunction with the accompanying drawings.

DETAILED DESCRIPTION

Figure 1:
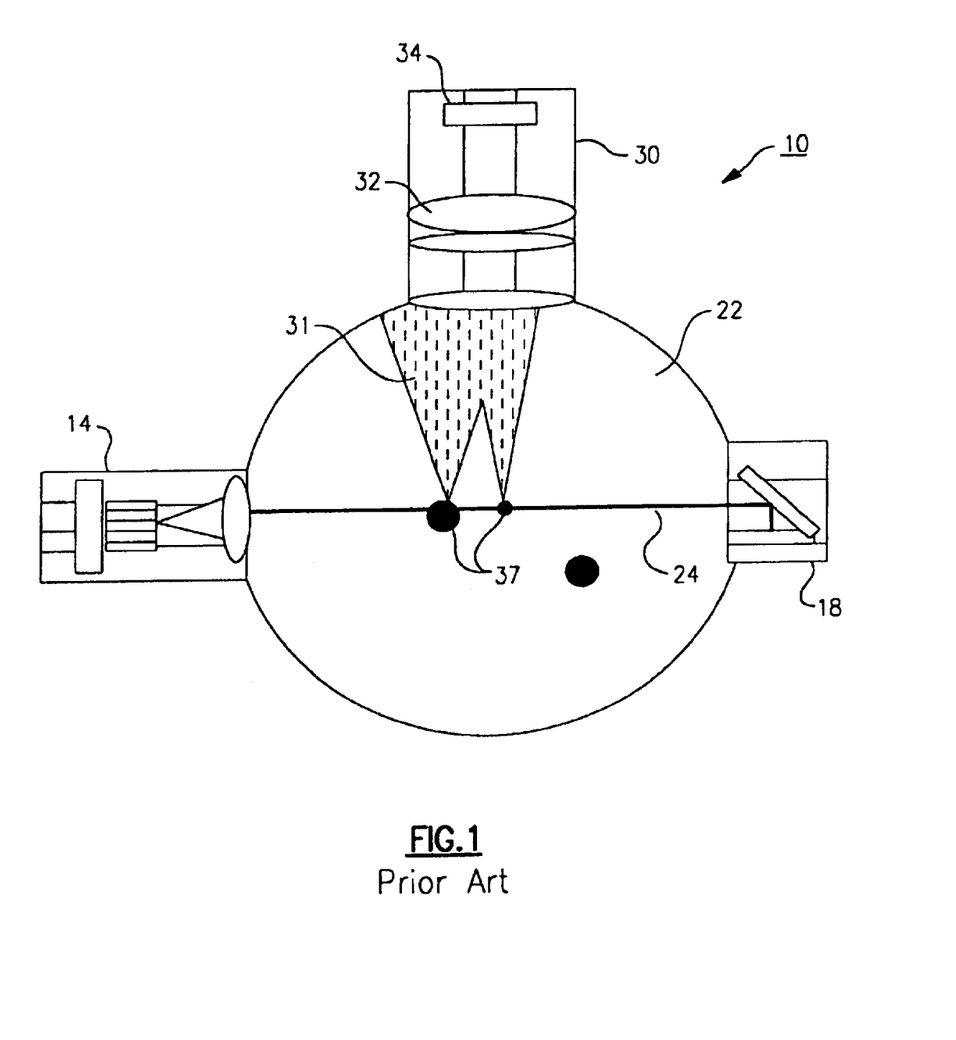
FIG. 1 is a pictorial representation of a known in situ particle measurement system.

Referring to FIG. 1, there is shown an ISPM (in situ Particle Measurement) system in accordance with the prior art. The system 10 includes a laser diode 14 which emits a fixed collimated light beam 24 across a measurement volume, such as a pump line 22. A beam dump 18 disposed oppositely from the laser diode 14 is used to collect the resulting light beam 24 in order to minimize background light. Particles 37 crossing the measurement volume cause the light beam 24 to back, forward or side scatter with the resulting light 31 being detected by an orthogonally arranged detector assembly 30 having a photocell 34 which receives focused scattered light through an collection optical system 32. Peak detection is employed on resulting voltage spikes from the scattered fixed beam to count particles over a preset threshold. As note, the light beam of the above ISPM system is fixed; therefore, the light beam can only impinge upon a particle moving through the measurement volume a single time.

Figure 2:
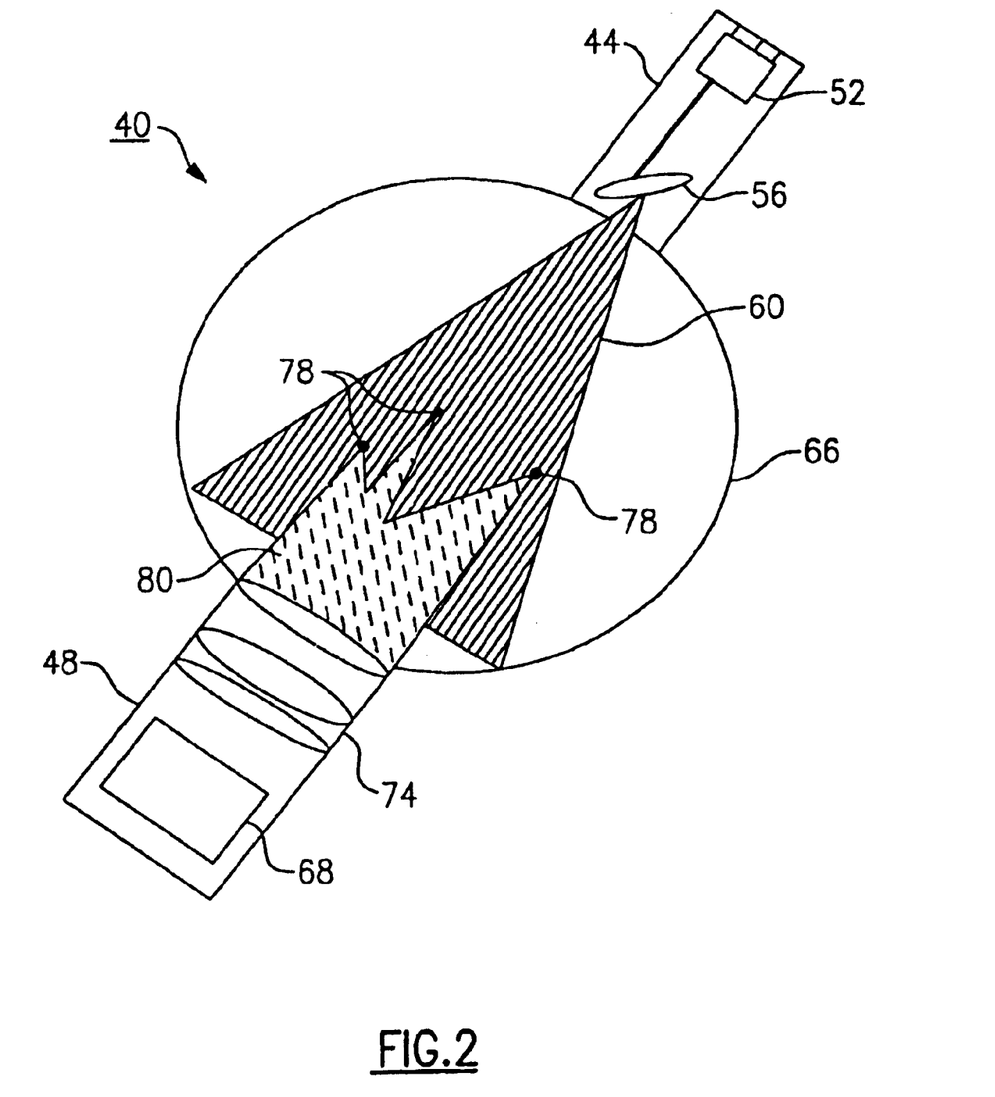
FIG. 2 is a pictorial representation of an in situ particle measurement system made in accordance with the present invention.

Referring to FIG. 2, there is pictorially shown an ISPM particle sensor assembly 40 in accordance with the present invention which can be used in conjunction with a semi-conductor processing apparatus. The above assembly 40 includes a transmitter 44 and a receiver 48.

The transmitter 44 includes a laser diode 52 as well as a scanning mirror 56 which is oscillated by a motor (not shown) wherein a resulting scanning laser beam 60 exits into a measurement volume, such as a pump line 66. The laser beam 60 sweeps the pump line 66 at a predetermined frequency.

The receiver 48 is arranged oppositely from the transmitter 44 and is arranged to receive the scanned laser beam 60. The receiver 48 includes a beam stop 70 that collects direct laser light. Particles 78 within the measurement volume scatter light from the scanned laser beam 60, shown as 80, which is directed through an set of collecting optics 74 to a photo-multiplier tube 68. As opposed to the previously illustrated detection system, particles can be impinged many times by the scanned laser beam 60, depending upon the particle's size and velocity.

Figure 3:
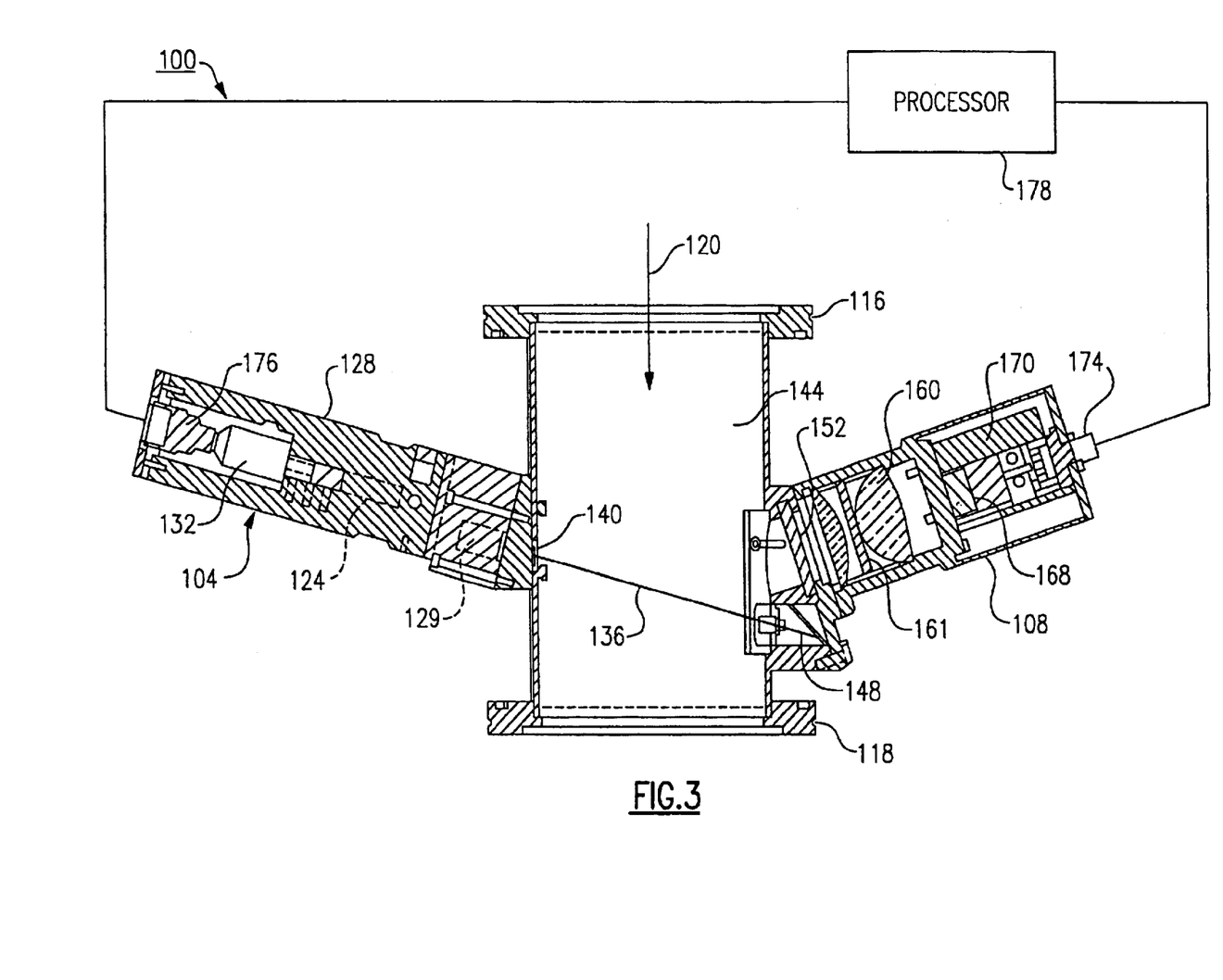
FIG. 3 is a partial sectioned side elevational view of a particle detecting system made in accordance with the invention.

FIG. 3 illustrates a more detailed version of the pictorial particle detector assembly of FIG. 2 in accordance with a preferred embodiment of the invention. The detector assembly 100 includes three interconnected major sections comprising a transmitter 104, a receiver 108 and a spool section 112 which interface with a processing tool (not shown). The spool section 112 is a cylindrical hollow pipe-like portion which includes flanges 116, 118 permitting the section to be attached to respective portions of the pump line of the processing tool. As shown herein, particles exiting from the tool's processing chamber (not shown) enter the pump line (not shown) and are directed through the spool section 112 as depicted by arrow 120.

The transmitter 104 includes a laser 124, such as a laser diode, which is arranged within a housing 128 as well as a scanning element 132, such as a rotating mirror, which is driven by a motor (not shown). Other optical means can be provided in lieu of a rotating mirror, such as a resonant scanner or other known means in order to create a scanned beam having a desired shape and orientation. According to this embodiment, the resulting laser beam 136 is scanned at 8 kHz, though it should be readily apparent that the scanner frequency and period of scan can easily be varied. The scanned laser beam 136 exits the transmitter 104 through a window 140 provided in the spool section 112. Details relating to the working and operation of the scanning element 132 are known and do not in and of itself form an essential part of the invention except where otherwise indicated herein. Additional mirrors (not shown) are positioned within the housing 128 which direct the scanned beam to the window 140 with stray light being reduced by means of a plurality of slits 129.

The receiver 108 includes a beam stop or dump 148 which is disposed along an optical path arranged diametrically opposite from the transmitter window 140. The receiver 108 also is defined by a housing 156 which includes a beam dump 148 and an adjacent window 152 which collects only scattered light from the laser beam 136 and directs same through a set of collection optics 160, including a spectral filter 161, toward a highly sensitive photo-multiplier tube 168 that is disposed adjacent to a proximal end of the receiver housing along with a suitable power supply 170. The light which is scattered from particles that are present in the measurement volume is therefore directed upwardly (according to FIG. 3) toward the photo-multiplier tube 168 while the majority of the remaining light not scattered by particles moving in the measurement volume is collected by the beam dump 148. Connectors 174, 176 on the proximal end of the receiver housing 156 and the transmitter housing 128, respectively, accommodate an inline signal processor 178 having a discriminator, peak detector and microprocessor having memory and appropriate software for performing postprocessing as described below. It should be noted that in lieu of the attached signal processor, alternately the pulse data, once discriminated, can alternately be stored onto a computer disk through a suitable interface (not shown) for offline post signal processing.

Since the scan velocity of the laser beam is considered high compared to the typical speed of a particle passing through the measurement volume, a typical particle will cause several pulses of scattered light while in the measurement volume. According to the present embodiment, the scan period of the laser is about 250 microseconds at 4 kHz.

Figure 4:
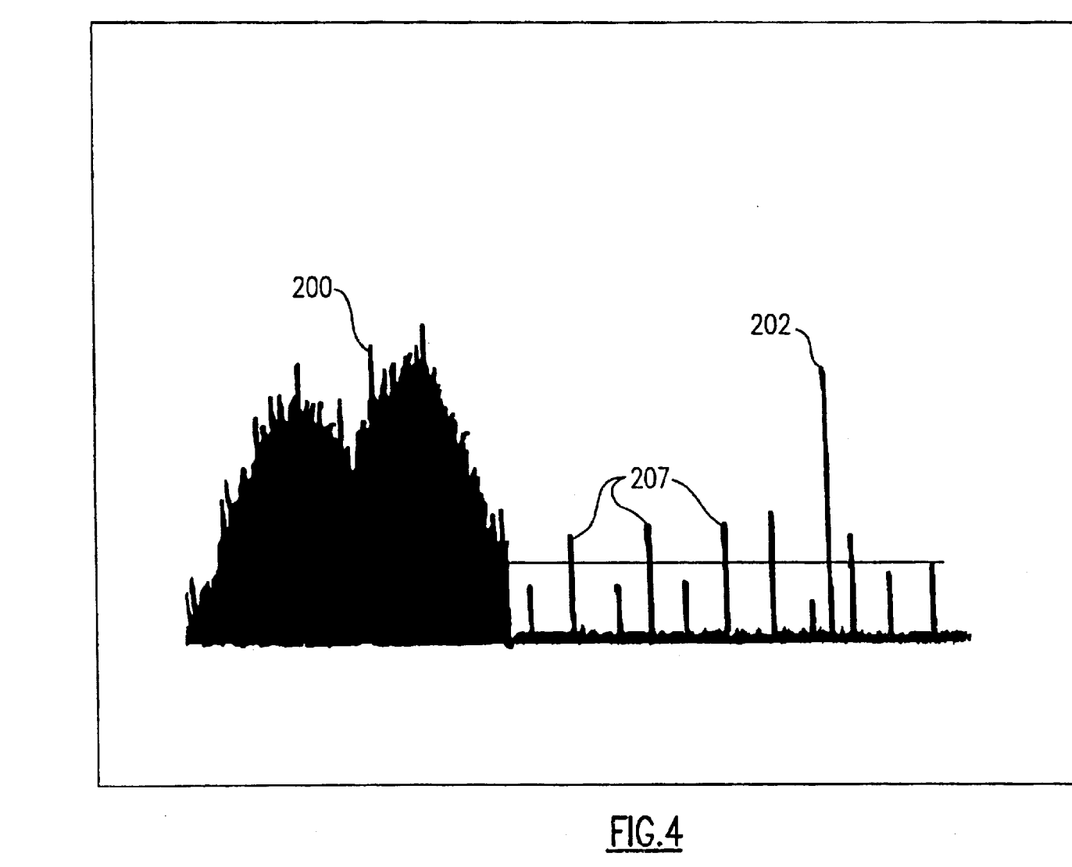
FIG. 4 is a graphical representation of multiple light scattering events as detected using the particle detecting system of FIGS. 2 and 3.

A typical representation is shown in FIG. 4, which depicts the various events that can occur with time being represented on the x-axis and photomultiplier voltage being expressed along the y-axis. Those events which can occur include electronic background noise, as caused by a myriad of sources such as vibration, optical noise (RF plasma) and optical interference due to the windows, among others, and particle scattering. Particles vary with speed and size, and therefore produce different light scattering pulse envelopes, such as 200 and 202. For example, it is difficult to discern between among the envelope of a medium sized high speed particle 202 and certain forms of noise, represented as 207.

To better scrutinize and isolate these events and to better eliminate false counts, a scattered light pulse train was empirically derived from an actual measurement using a sensor instrument such as that shown in FIG. 3, which is installed on a semi-conductor processing tool. Under these tool conditions, the worst case standard deviation of the background noise level was 50 mV, and the discrimination level was set to three times the background noise level (i.e. at 150 mV). The frequency of all of the scattering pulses rising above the discrimination level (defined as) empirically from data collected early in the process tool's maintenance cycle and near the close of the maintenance cycle. Based upon this data, the range off $f_{3\sigma}$ was found to lie between:

$$0.19 \text{ Hz} < f_{3\sigma} < 1.86 \text{ Hz}$$

with an average $f_{3\sigma}$ of 0.86 Hz. Note that this false count rate also includes valid particle signals that will also survive the signal-processing algorithm. Consequently, this calculated false count rate is a worst case assessment of the impact from background noise levels.

Figure 10:
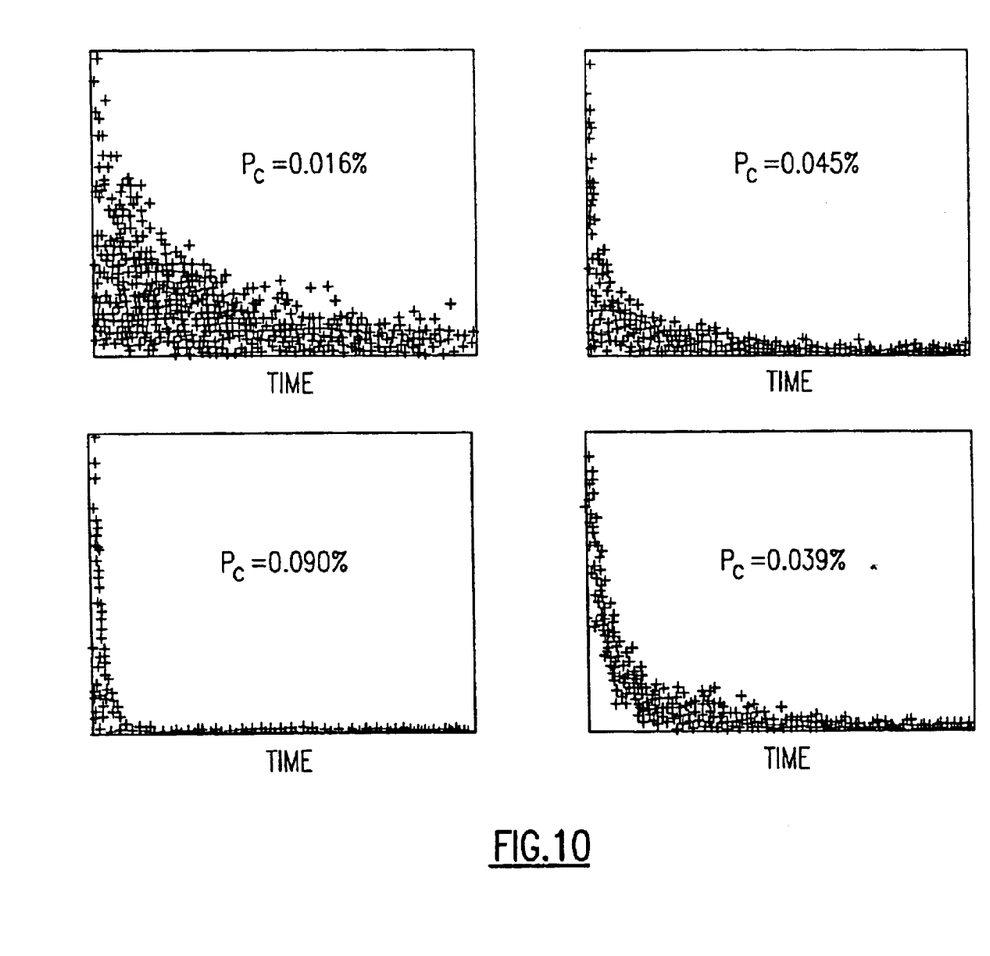
FIG. 10 is a graphical representation of a series of scattering pulse amplitude distributions.

The distributions of scattering pulses for four separate production runs or lots are shown in FIG. 10. Increasing time is represented on the x-axis while increasing pulse amplitude is shown on the y-axis. These scattering amplitude distributions include both signal and noise pulses. However, it is observed that the "noise" pulses will dominate the shape of the distribution, since there are ~100 or more noise pulses that occur for each signal pulse.

As discussed previously, the present signal-processing algorithm accepts any pulse which correlates to another pulse within 250±10 μs which as noted above is the period of the scanning mirror. Calculating the area under the Poisson curve between 245 μs and 255 μs (and normalizing it with the total area under the curve) yields the probability of two noise pulses correlating together at the scanner frequency ($P_c$), given as:

$$P_c = \frac{\int_{245\mu s}^{255\mu s} F_p(s) ds}{\int_0^\infty F_p(s) ds}$$

where "$F_p(s)$" is the Poisson distribution function and "s" is the spacing of the scattering pulses. The probability of two noise pulses occurring together (based upon the scattering amplitude distributions shown in Figure) is summarized for four different product lots in Table 1.

TABLE 1

Probability of Two Noise Pulses

| Lot # | Probability ($P_c$) |
|---|---|
| 2 | 0.016% |
| 4 | 0.045% |
| 5 | 0.090% |
| 9 | 0.039% |
| Average | 0.048% |

The frequency of correlated noise pulses over the discrimination level (which is set at three times the background noise level), $f_{3\sigma}$, is given by:

$$f_{c3\sigma} = f_{3\sigma} \times (Pc)^{n-1}$$

where "$f_{3\sigma}$" is the frequency of correlated noise pulses rising above the discrimination level, and "n" is the number of correlated pulses within the pulse train. The frequency of correlated noise pulses, and the number of false counts that will occur within a product lot (of 25 wafers), is tabulated in Table 2 for the cases of two-, three-, and four-correlated pulses.

TABLE 2

Prediction of False Count Rates

| # Correlated Pulses | Frequency ($f_{c3\sigma}$) (Hz) | Expected Number of False Counts Per Lot* |
|---|---|---|
| 2 pulses | $4.1 \times 10^{-4}$ | 2.9 |
| 3 pulses | $2.0 \times 10^{-7}$ | $1.3 \times 10^{-3}$ |
| 4 pulses | $9.5 \times 10^{-11}$ | $6.3 \times 10^{-7}$ |

*Two hour lot duration assumed

This analysis indicates that the maximum false count rate is less than three false counts per lot (~0.1 false counts per wafer), when the discrimination level is set at three times the standard deviation of the background noise level (e.g., at a 3:1 signal-to-noise level). If the discrimination level is raised even higher (from 150 mV to 300 mV), the resulting false alarm rate is predicted to decrease by over two orders of magnitude. Alternately, the false alarm rate can be improved by nearly three orders of magnitude, by requiring at least three correlated pulses to be detected (versus two correlated pulses) for a particle count to be discriminated from the background noise levels.

It has been further demonstrated that a discriminator setting of four times the standard deviation of the noise will provide sufficient protection against false alarms. This can be more easily accomplished by setting the discriminator with respect to the highest observed standard deviation for the entire process (typically this is the chamber clean) at the expense of size sensitivity. However, to maintain maximum sensitivity over the entire process, it will be necessary to periodically auto-set the discriminator. This can be easily accomplished by temporarily reducing the discriminator, taking a sample of the noise, calculating the standard deviation and setting the discriminator to four times the measured standard deviation. This technique will account for all changes in noise, whatever the cause (RF, dirty windows, electronics problems, etc).

Figure 11:
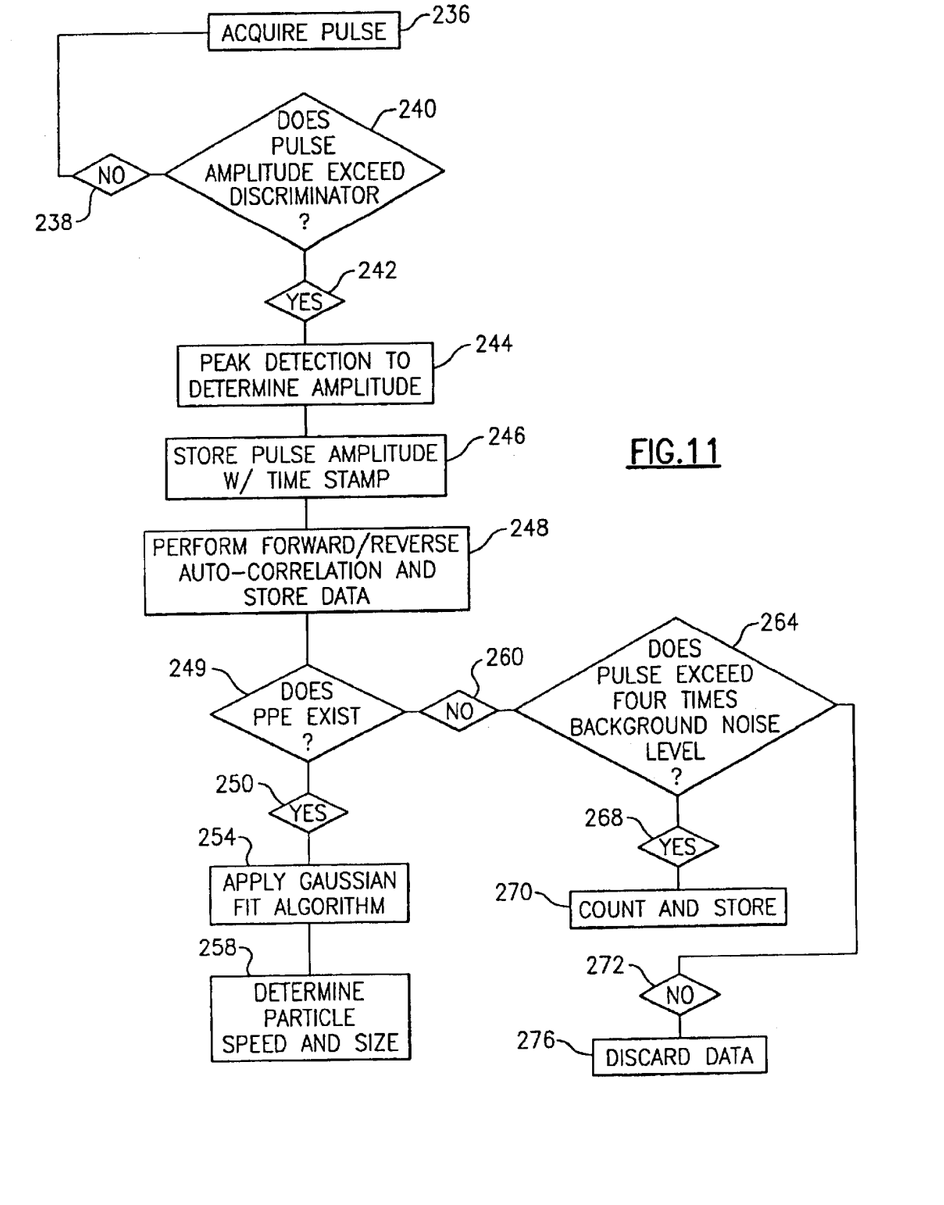
FIG. 11 is a flowchart indicating the method in accordance with an embodiment according to the present invention.

A method according to the invention is described according to the flowchart shown in FIG. 11. According to the method, the light pulses that are scattered by each scanned particle crossing through the measurement volume are initially detected by a photo-multiplier 168, step 236. The electrical current output from the photo-multiplier 168 is then converted by conventional means into a voltage pulse, which is subsequently amplified such as for example, by means of a high-speed, two stage analog amplifier. A level-triggering device, such as a discriminator, step 240, eliminates those signals that do not exceed a minimum threshold value, step 238.

Figure 7:
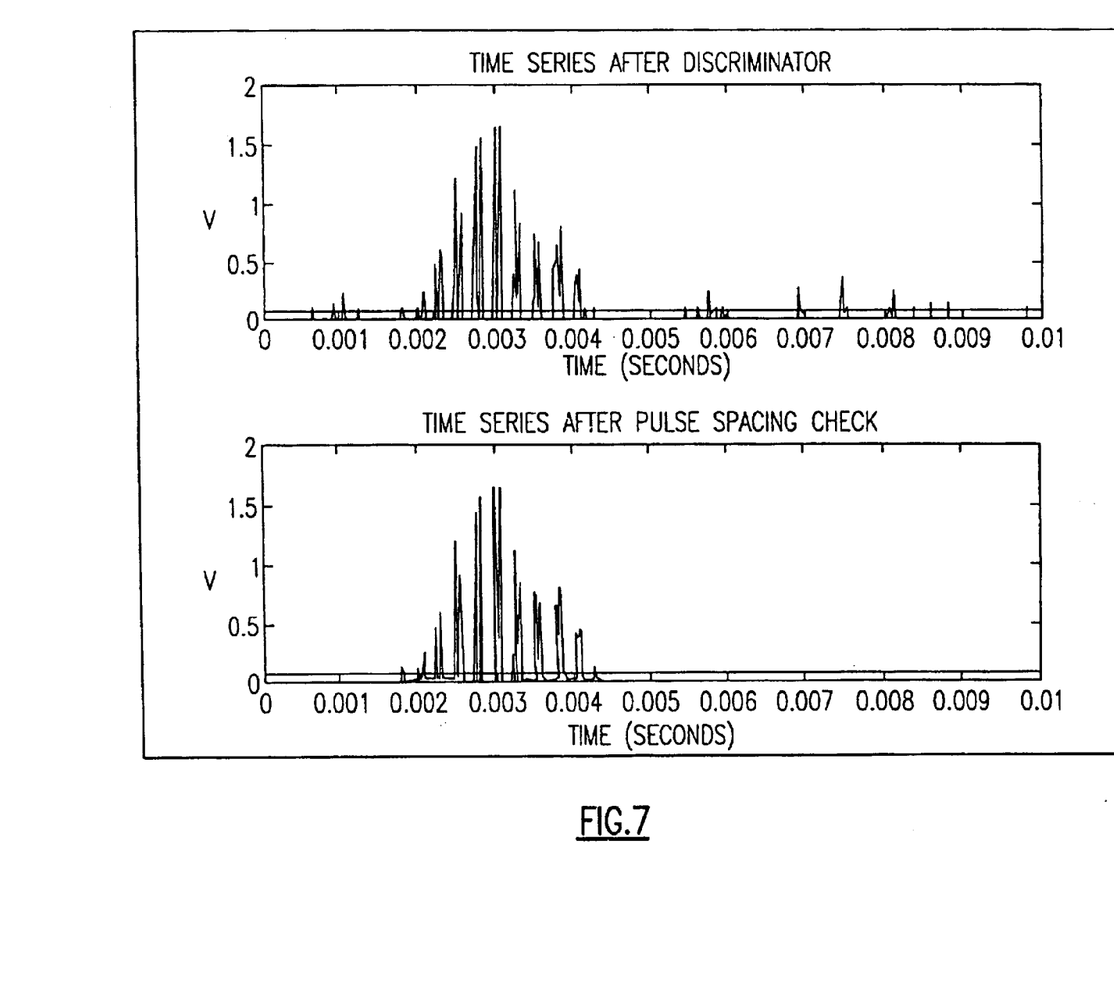
FIG. 7 is a graphical representation of filtered and non-filtered noise pulses in the time domain.

The affect of this algorithm is illustrated in FIG. 7. The upper data window of this figure illustrates a discriminated pulse stream, in which noise pulses failing to reach a predetermined threshold value (e.g. 100 mV) having been filtered from consideration. The lower window of this figure depicts the data as it has been filtered in the time domain. The only data that remains in the lower window is that replicated at the 4 kHz scan rate.

The pulse train exiting the discriminator is analyzed with a peak-detector, each contained within the processor 178 to determine the maximum value of the pulse, step 244. Details for performing this operation are well known in the field and require no further discussion herein. This value, as well as the pulse time stamp (micro-second resolution) is stored, step 246, for example, on a computer hard disk or in the memory of a microprocessor of the processor 178, for post processing using a preferred signal-processing technique which is described below.

The present method determines whether the pulse is representative of a particle in the scanned measurement volume by determining whether or not the pulse is part of a PPE (a pulse-particle envelope) and generating the envelope if one does exist. This determination is accomplished by looking either ahead and/or behind a representative first pulse which has been time-stamped and then utilizing the microprocessor to evaluate the scattered light distribution to locate a second pulse that lags and/or leads the first pulse by substantially the scanner period for a particular time period window.

Figure 8:
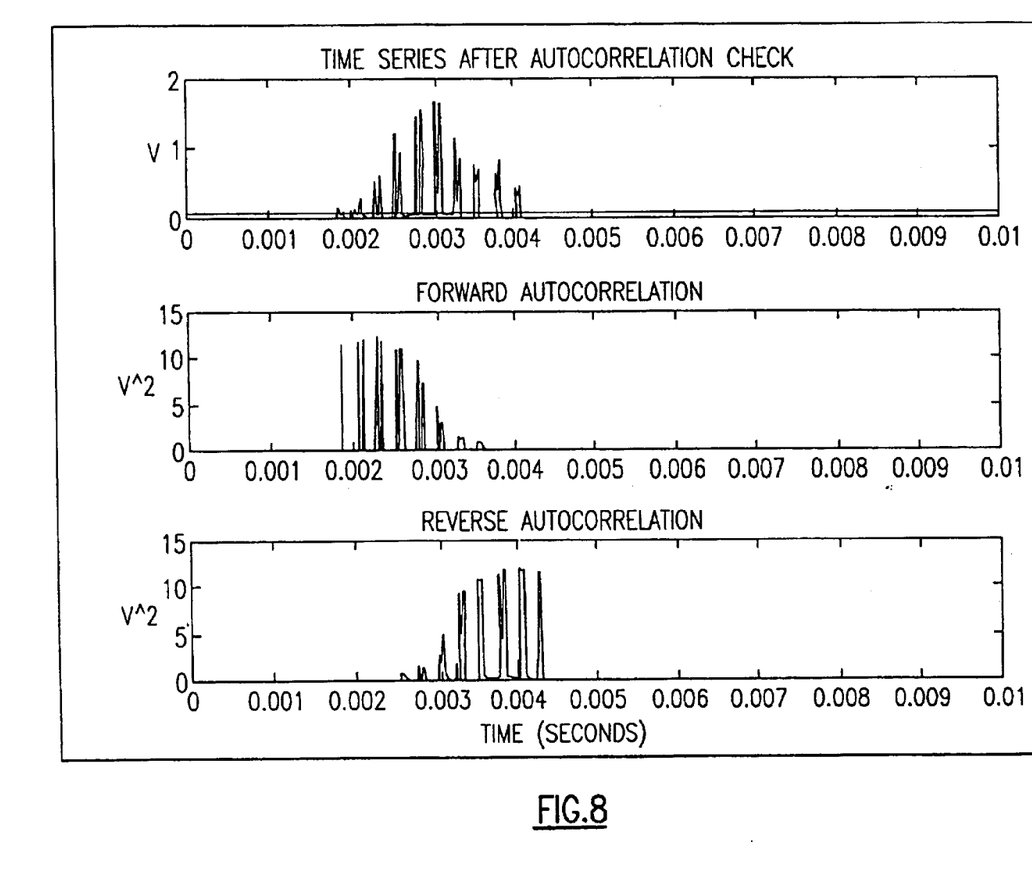
FIG. 8 is a typical pulse envelope and forward and reverse autocorrelation so as to identify the start and end of the pulse particle envelope.

After the removal of noise pulses, the signal-processing algorithm begins searching for PPE's. According to the present method, FIG. 11, an autocorrelation calculation is performed in the forward and reverse directions (again in the time domain), step 248, in order to identify the beginning and end of an individual PPE using the microprocessor. For purposes of discernment for the embodiment shown in FIG. 3, the 4 kHz scanner frequency is selected having a 250 $\mu$s period (+/−10 $\mu$s) in order to perform the autocorrelation. As shown in FIG. 8, and at the onset of an exemplary PPE, the autocorrelation is high in the forward direction and zero in the reverse autocorrelation. Conversely and at the end of the envelope, autocorrelation is high in the reverse direction and zero in the forward direction. The autocorrelation calculation must be performed over a time period that avoids inclusion of subsequent particle scattering envelopes. In this particular instance, a two milliseconds (0.002 sec) time period was selected. The selection of an appropriate period is somewhat arbitrary and can be tailored to particle concentration and data rate.

Figure 5:
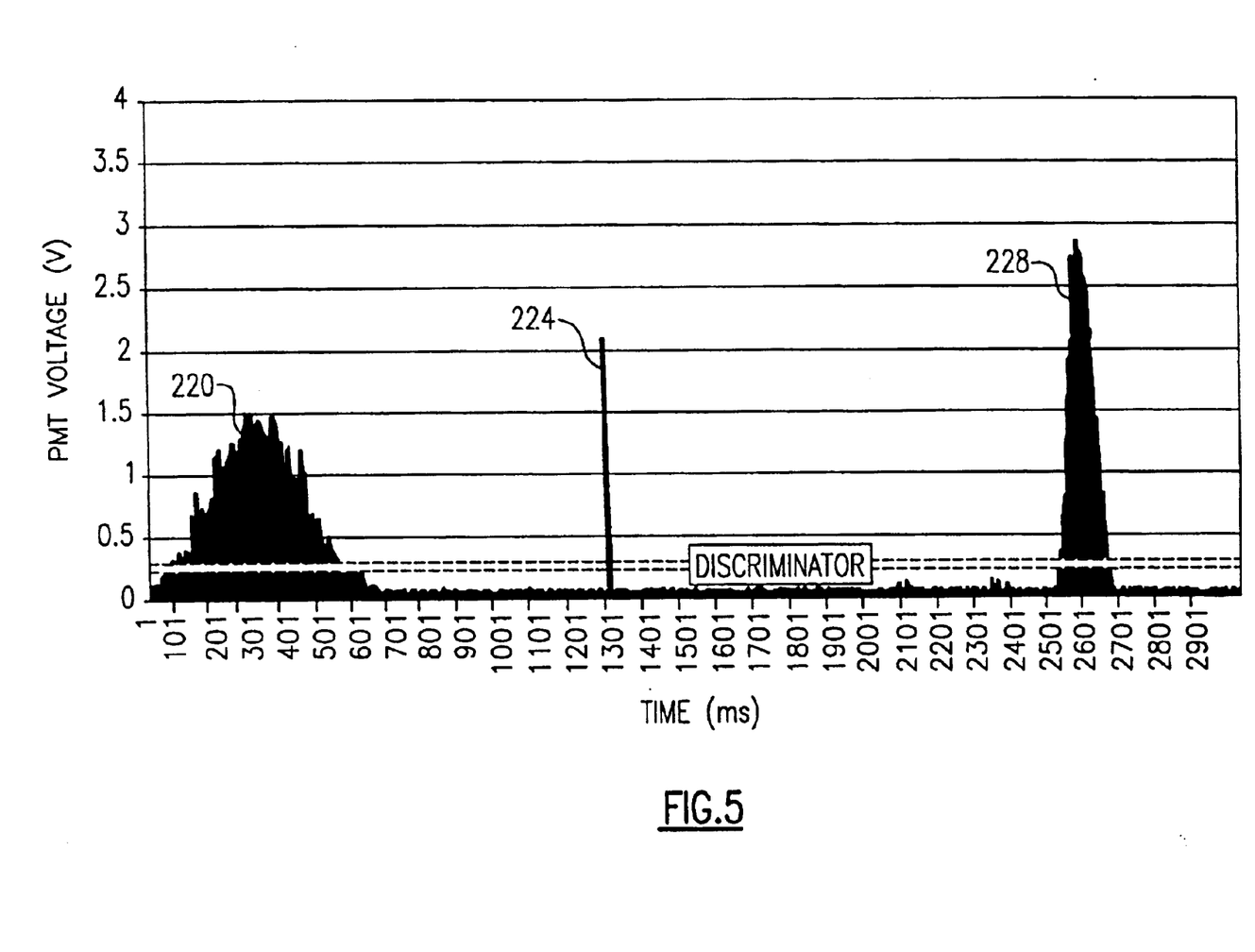
FIG. 5 is a graphical representation of typical pulse-particle envelopes detected using the system of FIGS. 2 and 3.

Through this approach, the beginning and end of the particle-pulse envelope (PPE) can be identified. A set of typical PPEs are illustrated in FIG. 5. As shown in this Figure, these envelopes can take on different forms, depending on the speed (e.g., velocity) of the particle as well as the size thereof. As shown, an envelope for a relatively small and slow moving particle is shown as 220, with a medium sized and faster moving particle having a much narrower profile 224 (envelope) and a particle having a larger size (diameter) and moderate speed such as 228 being shown for contrast.

Figure 9:
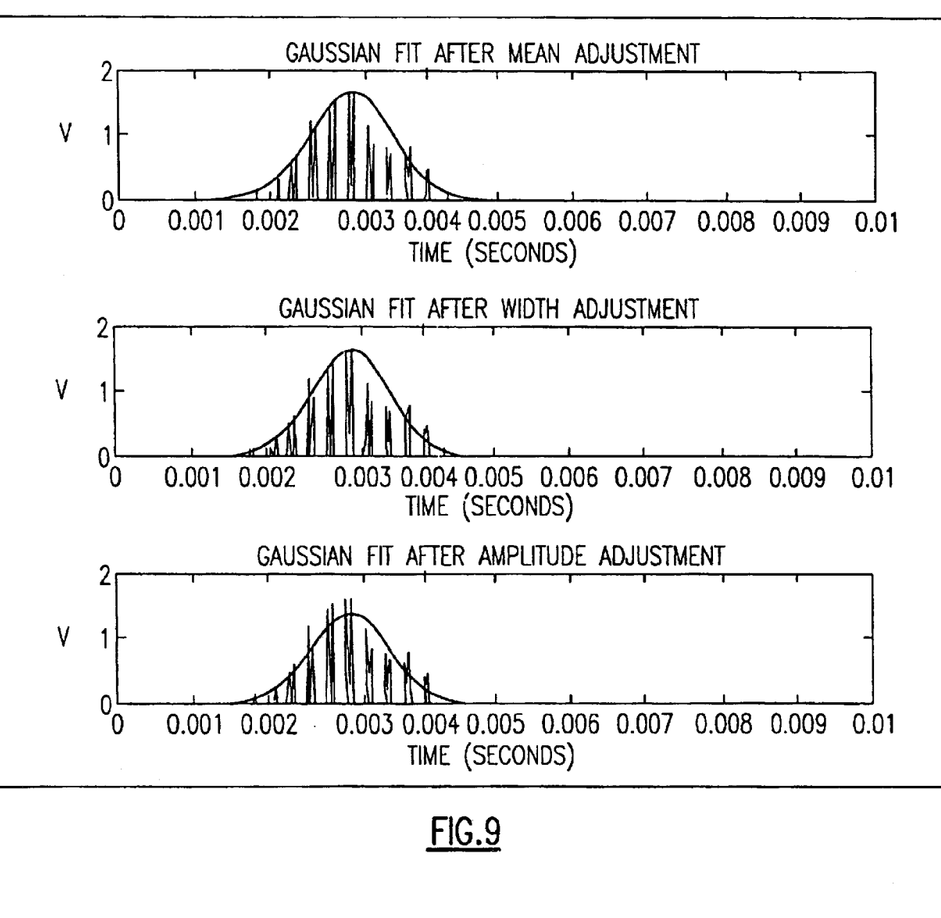
FIG. 9 is a typical pulse particle envelope and an associated Gaussian fit adjusted for mean, width, and amplitude adjustments, respectively thereof.

Referring to FIGS. 9 and 11, after the particle-pulse envelope has been identified as in the preceding auto-correlation calculation, step 254, a Gaussian fitting routine is applied. Specific details relating to performing this type of statistical fit are known in the field. The algorithm begins with an assumed Gaussian mean, width, and amplitude. Each of these values are subsequently iterated to produce minimum error between the peak pulse amplitudes and the value of the Gaussian fit. The fitting procedure for the mean, width and amplitude is illustrated in FIG. 9. The deficiency of the above algorithm is that it only finds the local minimum error. However, if one considers the prohibitively long calculation required to determine a global minimum of three variables, and the fact that high accuracy is not required for these variables, the local minimum approach becomes more attractive. The created Gaussian fit should preserve the maximum pulse amplitude observed in the particle-pulse envelope. This is also a valid approach that could be used to suitably modify the algorithm described previously.

Figure 6:
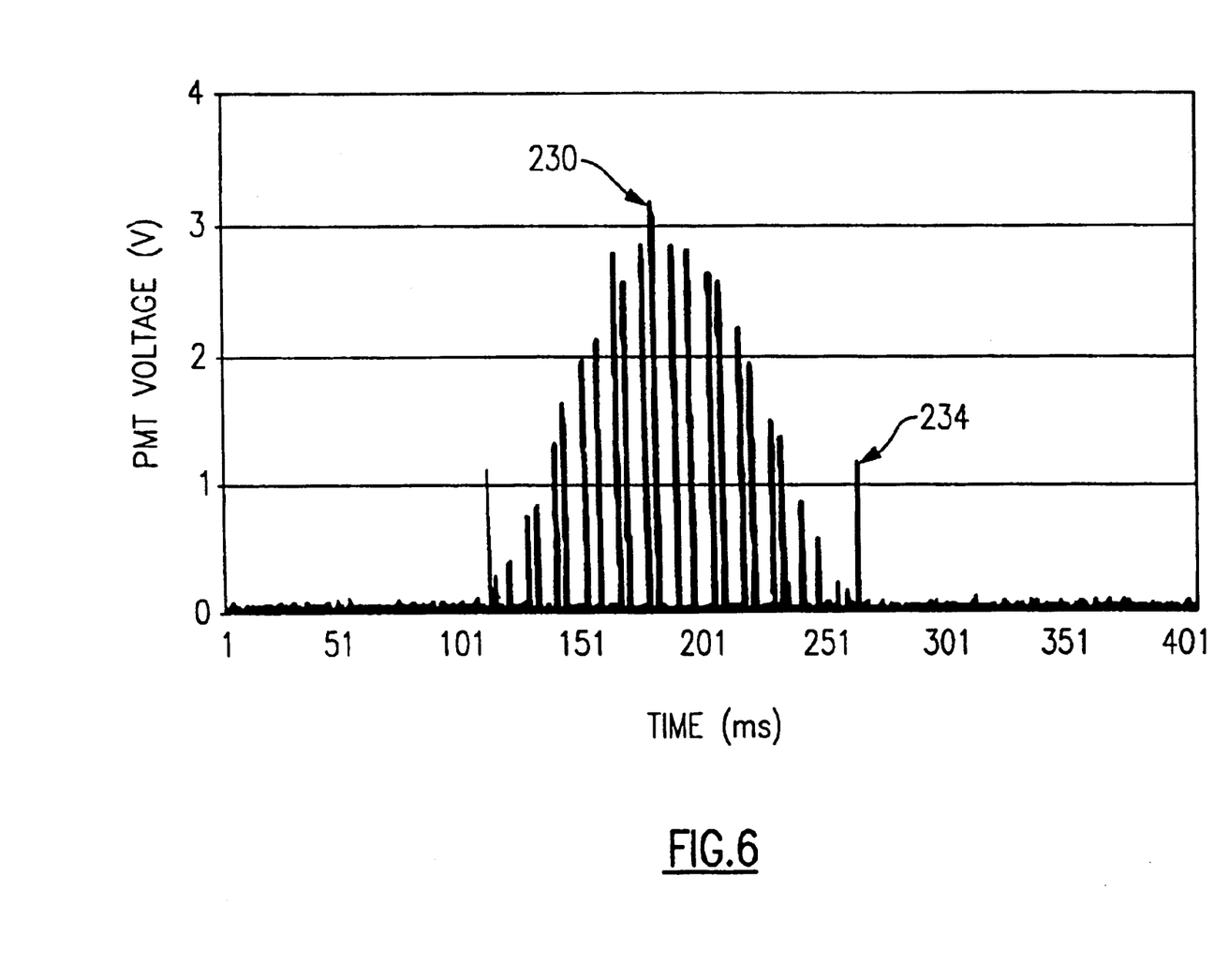
FIG. 6 is an enlarged graphical representation of a pulse-particle envelope using the processing method of the present invention.

As noted, the Gaussian fit once obtained on each of the particle-pulse envelopes, can lead to a valid determination of particle size and velocity, step 258. Once the fit is obtained, the peak amplitude 230 of the Gaussian fit is used to determine particle size while the width 240 of the envelope is determinative of speed as shown in FIG. 6. More particularly, the slope of the Gaussian fit as coupled with the diameter of the laser beam at the sample volume is used to determine particle speed. One known technique for determining speed using a Gaussian fit is disclosed for example, in Holve, D. J. entitled: "Transit Timing Velocimetry (TTV) for Two-Phase Reacting Flows", Combustion and Flame, 48:105 (1982), the entire contents of which are herein incorporated by reference.

Referring to FIG. 11, one exception must be made to the autocorrelation algorithm described above. This exception refers to extremely fast particles which are contacted by the scanning beam a single time and therefore do not produce a pulse particle envelope (PPE). These events must still be validly counted by the above apparatus and distinguished from the noise produces by RF, optical and electronic effects and other means. According to this exception and as described above, the signal processing algorithm does not throw out uncorrelated peaks if the amplitude of the peaks is four times larger than the background noise level. The probability of the noise rising above this high, even during chamber clean, is extremely negligible and is a 12 sigma event. As shown in the flowchart and after if has been determined that the peak is uncorrelated, step 260, a determination is made as to whether the pulse amplitude exceeds four times the background level to be distinguished as a single pulse event (a particle), step 264. If yes, step 268, the data is stored and the particle is validly counted, step 270. If no, step 272, then the data is discarded, step 276.

In closing, we further note the following supporting documents which are herein cross-referenced incorporated by reference in their entirety:

1. P. G. Borden, (1990) 'Monitoring Particles in Production Vacuum Process Equipment Part 1: The Nature of Particle Generation', Microcontamination, 8(1): p. 21–24, 56–57.

2. P. G. Borden (1990) 'Monitoring Particles in Production Vacuum Process Equipment Part 2: Implementing a Continuous Real-Time Program', Microcontamination, 8(2): p. 23–27, 61.

3. P. G. Borden (1990) 'Monitoring Particles in Production Vacuum Process Equipment: Data Collection, Analysis, and Subsequent Action for Process Optimization', Microcontamination, 8(3): p. 47–51.

4. P. G. Borden (1991) 'Monitoring Vacuum Process Equipment: In Situ Monitors—Design and Specification', Microcontamination, 9(1): p. 43–47.

5. Holve, D. J. "Transit Timing Velocimetry (TTV) for Two-Phase Reacting Flows." Combustion and Flame, 48:105 (1982).

Parts List for FIGS. 1–11
10 system
14 diode
18 beam dump
22 pump line
24 light beam
30 detector assembly
31 scattered light
32 collection optics
34 photocell
37 particles
40 assembly
44 transmitter
48 receiver
52 laser diode
56 scanning mirror
60 laser beam
66 pump line
68 photo-multiplier tube
70 beam stop
74 collecting optics
78 particles
80 scattered light
100 detector assembly
104 transmitter
108 receiver
112 spool section
116 flange
118 flange
120 arrow
124 laser
128 housing
129 slits
132 scanning element
136 laser beam
140 window
144 measurement volume
148 beam dump
152 window
160 collection optics
168 photo-multiplier tube
170 power supply
174 connector
176 connector
178 processor
200 particle pulse envelope
202 particle pulse envelope
207 noise pulse
220 envelope
224 envelope
228 envelope
230 peak amplitude
234 envelope width
236 step
238 step
240 step
242 step
244 step
246 step
248 step
249 step
250 step
254 step
258 step
260 step
264 step
268 step
270 step
272 step
276 step While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A method for processing a scattered light signal to determine the presence of particles in a scanned measurement volume, said method comprising the steps of:

applying a scanning light beam onto a measurement volume;

detecting scattered light pulses from particles moving through said measurement volume; and processing the detected light pulses, including the steps of:

determining the existence of multiple pulse events representative of a scanned particle in a time domain by generating a corresponding particle pulse envelope (PPE) in order to segregate particles moving in the measurement volume from noise; said envelope generating step including steps of:

identifying a second pulse adjacent to a first pulse in the time domain, said second pulse being spaced substantially one scanner period from said first pulse; and identifying a plurality of pulses adjacent to said first and second pulses indicative of a pulse envelope representative of a single particle in said measurement volume wherein said step of identifying a plurality of pulses includes the steps of forward and reverse autocorrelating said pulses over a predetermined time period to determine the size of said pulse envelope.

2. A method according to claim 1, including the step of:

segregating single pulse events as detected light pulses for purposes of counting particles in said measurement volume.

3. A method according to claim 2, wherein said segregating step includes the step of determining if the pulse amplitude exceeds a discriminator threshold setting.

4. A method according to claim 3, wherein the discrimination threshold setting is set to at least three times that of background noise level.

5. A method according to claim 3, wherein the discrimination threshold setting is set to at least four times that of background noise level.

6. A method according to claim 1, including the steps of:
converting the light pulses into electrical pulses; and
processing the converted electrical pulses in the time domain to detect the existence of multiple pulses indicative of a particle being multiply contacted by the scanning light beam.

7. A method according to claim 6, including the step of discriminating all converted electrical pulses and filtering all pulses falling below a predetermined threshold.

8. A method according to claim 7, including the step of determining the peak amplitudes of the converted electrical pulses.

9. A method according to claim 1, including the step of applying a Gaussian fit to said pulse envelope.

10. A method according to claim 9, including the step of measuring the peak amplitude of the pulse envelope to determine the size of the particle.

11. A method according to claim 9, including the step of measuring the width of the pulse envelope to determine the speed of the particle.

12. A method according to claim 1, wherein said method is performed in a process chamber.

13. A method according to claim 1, wherein said method is performed in a pump line of a processing tool.

14. A method according to claim 1, wherein said method is performed on line.

15. A method according to claim 1, including the step of storing the pulse values and performing each of the processing steps remotely from detection apparatus.

16. A method for distinguishing noise from particle counts in a scattered light beam, said process including the steps of:
transmitting a light beam into a measurement volume containing particles of varying speed and size;
detecting at least one scattered light pulse from said measurement volume;
converting said at least one light pulses into an electrical signal;
determining the amplitudes of said at least one pulse;
counting said pulse if the amplitude of said at least one pulse exceed a threshold discriminator threshold which is equal to at least three times the highest value of a background noise level.

17. A method according to claim 16, wherein said threshold level is equal to at least four times the highest value of the background noise level.

18. A method for processing a scattered light signal to determine the presence of particles in a scanned measurement volume, said method comprising the steps of:
applying a scanning light beam onto a measurement volume;
detecting scattered light pulses from particles moving through said measurement volume; and
processing the detected light pulses, including the step of determining the existence of multiple pulse events representative of a scanned particle in a time domain by generating a corresponding particle pulse envelope (PPE) in order to segregate particles moving in the measurement volume from noise, said method further including the step of counting pulses having an amplitude exceeding a threshold discriminator threshold which is equal to at least three times the highest value of a background noise level.

19. A method for effectively measuring particles passing through a measurement volume, said process including the steps of:
scanning a light beam into said measurement volume at a predetermined frequency;
detecting light pulses scattered from the moving particles; and
determining the presence of pulse envelopes indicative of multiple contacts with a particle over a scanning period by:
identifying a second pulse adjacent to a first pulse in a time domain, said second pulse being spaced substantially one scanner period from said first pulse; and
identifying a plurality of pulses adjacent to said first and second pulses indicative of a pulse envelope representative of a single particle in said measurement volume by forward and reverse autocorrelating said pulses over a predetermined time period to determine the size of said pulse envelope.

20. A method according to claim 19, including the step of:
segregating single pulse events as detected light pulses for purposes of counting particles in said measurement volume.

21. A method according to claim 20, wherein said segregating step includes the step of determining if the pulse amplitude exceeds a discriminator threshold setting.

22. A method according to claim 21, wherein the discrimination threshold setting is set to at least three times that of the background noise level.

23. A method according to claim 21, wherein the discrimination threshold setting is set to at least four times that of the background noise level.

24. A process according to claim 19, including the steps of:
converting the light pulses into electrical pulses; and
processing the converted electrical pulses in a time domain to detect the existence of multiple pulses indicative of a particle being multiply contacted by the scanning light beam.

25. A method according to claim 24, including the step of discriminating all converted electrical pulses and filtering all pulses falling below a predetermined threshold.

26. A method according to claim 25, including the step of determining the peak amplitudes of the converted electrical pulses.

27. A method according to claim 19, including the step of applying a Gaussian fit to each said determined pulse envelope.

28. A method according to claim 27, including the step of measuring the peak amplitude of each pulse envelope to determine the size of the corresponding particle.

29. A method according to claim 28, including the step of measuring the width of each pulse envelope to determine the speed of the corresponding particle.

30. A method according to claim 19, wherein said method is performed in a process chamber.

31. A method according to claim 19, wherein said method is performed in a pump line of a processing tool.

32. A method according to claim 19, wherein said method is performed on line.

33. A method according to claim 19, including the step of storing the detected pulse values and performing each of the processing steps remotely from detection apparatus.

* * * * *